United States Patent
Iwamoto et al.

(10) Patent No.: US 6,281,362 B1
(45) Date of Patent: Aug. 28, 2001

(54) METHOD FOR PRODUCING PYRIDINE BASES

(75) Inventors: Keisuke Iwamoto, Ichihara; Takayuki Shoji, Osaka; Yoko Nakaishi, Sodegaura, all of (JP)

(73) Assignee: Koel Chemical Company, Ltd., Osaka (JP)

( * ) Notice: Subject to any disclaimer, the term of this patent is extended or adjusted under 35 U.S.C. 154(b) by 0 days.

(21) Appl. No.: 09/599,956

(22) Filed: Jun. 23, 2000

(51) Int. Cl.$^7$ .................................................. C07D 211/72
(52) U.S. Cl. ............................................................. 546/345
(58) Field of Search ................................................ 546/345

(56) References Cited

U.S. PATENT DOCUMENTS

| | | |
|---|---|---|
| 4,220,783 | 9/1980 | Chang et al. . |
| 4,285,811 * | 8/1981 | Miyake . |
| 4,810,794 | 3/1989 | Shimizu et al. . |
| 4,866,179 | 9/1989 | Cheng et al. . |
| 4,960,894 * | 10/1990 | Hoelderich . |
| 5,218,122 * | 6/1993 | Goe . |
| 5,780,635 * | 7/1998 | McAteer . |

FOREIGN PATENT DOCUMENTS 9003366  4/1990  (WO) .

OTHER PUBLICATIONS

CA 123:267577, abstract by Guo,, Cuihua Zuebao, 16(5), pp. 420–424, 1995.*
CA 121:188342, abstract of Guo, Cuihua Zuebao, 15(4), pp. 309–313, 1994.*
CA 118:62594, abstract of Becker, DE 4116630, 1992.*
CA 103:187220, abstract of Pang, Huazue Zuebao, 43(8), pp. 739–744, 1985.*
Sudhakar Reddy J. et al; "Synthesis, Characterization, and Catalytic Properties of a Titanium Silicate, TS–2, with Mel Structure"; Journal of Catalysis, US, Academic Press, Duluth, MN, vol. 130, No. 2, Aug. 1, 1991, pp. 440–446.

* cited by examiner

Primary Examiner—D. Margaret Seaman
(74) Attorney, Agent, or Firm—Stevens, Davis, Miller & Mosher, L.L.P.

(57) ABSTRACT

A method for producing pyridine bases which gives improved yield and comprises reacting in a gas-phase an aliphatic aldehyde, aliphatic ketone or mixture thereof with ammonia in the presence of a zeolite containing titanium and/or cobalt and silicon as zeolite constituent elements in which the atomic ratio of silicon to titanium and/or cobalt is about 5 to about 1000.

8 Claims, No Drawings

METHOD FOR PRODUCING PYRIDINE BASES

BACKGROUND OF THE INVENTION

The present invention relates to a method for producing pyridine bases by reacting in a gas-phase an aliphatic aldehyde, aliphatic ketone or mixture thereof with ammonia in the presence of a catalyst.

A method for producing pyridine bases by reacting in a gas-phase an aliphatic aldehyde, aliphatic ketone or mixture thereof with ammonia in the presence of a catalyst is known. Various methods are reported, for example, a method in which an amorphous silica-alumina is used as a catalysts, a method in which zeolites such as aluminosilicate and the like are used, as well as other methods. Among the catalysts, zeolite is suitable as a catalyst for producing pyridine bases in which a gas-phase reaction is conducted under high temperature condition, due to its excellent heat-resistance.

As the zeolite used as a catalyst for producing pyridine bases, for example, heteosilicate such as ferrosilicate, borosilicate and gallosilicate, in addition to aluminosilicate, are known. These zeolites are used singly as a catalyst. Alternatively, they are allowed to contain an ion and/or compound of various elements, such as copper, zinc, cadmium, bismuth, chromium, molybdenum, tungsten, cobalt, nickel, ruthenium, rhodium, palladium, iridium and the like, to give a catalyst to be used.

In the production of pyridine bases, it is known that main products, the pyridine bases, are determined by combination of the raw materials, an aliphatic aldehyde and an aliphatic ketone. Typical examples of them are shown in Table 1.

TABLE 1

| Raw materials (Aliphatic aldehyde, Aliphatic ketone) | Main Product (Pyridine bases) |
| --- | --- |
| Acetaldehyde | α-picoline + γ-picoline |
| Acetaldehyde + formaldehyde | Pyridine + β-picoline |
| Acrolein | β-picoline |
| Acrolein + acetaldehyde | Pyridine |
| Acrolein + propionaldehyde | β-picoline |
| Propionaldehyde + formaldehyde | 3,5-lutidine |
| Crotonaldehyde + propionaldehyde | 3,4-lutidine |
| Crotonaldehyde + acetone | 2,4-lutidine |
| Formaldehyde + acetone | 2,6-lutidine |
| Acetone | 2,4,6-collidine |
| Methacrolein + methyl ethyl ketone | 3,5-lutidine + 2,3,5-collidine |

As described above, various pyridine bases can be produced by reacting in a gas-phase an aliphatic aldehyde, aliphatic ketone or mixture thereof with ammonia in the presence of a zeolite as a catalyst. However, the yields of pyridine bases produced by conventional methods are yet low.

For example, in the comparative examples described below, which were conducted by the present inventors and in which acetaldehyde is reacted with ammonia to produce α-picoline and γ-picoline according to the above-described conventional methods, namely, by using aluminosilicate, ferrosilicate or the like as the catalyst, the yields of α-picoline and γ-picoline were, respectively, 17.6% and 18.5% when aluminosilicate was used, 18.6% and 17.5% when ferrosilicate was used, and 17.3% and 19.3% when gallosilicate was used.

Thus, the yields of the intended pyridine bases in conventional methods are not yet satisfactory, and further improvement in the yield is desired.

The present inventors have intensively studied for finding a method that can produce pyridine bases in higher yield. As a result, the present inventors have found that, when pyridine bases are produced by reacting in a gas-phase an aliphatic aldehyde, aliphatic ketone or mixture thereof with ammonia in the presence of a zeolite containing titanium and/or cobalt and silicon as zeolite constituent elements in which the atomic ratio of silicon to titanium and/or cobalt is about 5 to about 1000, pyridine bases can be produced at higher yield as compared with the conventional case in which a zeolite such as aluminosilicate, ferrosilicate or the like is used as the catalyst. Thus, the present invention has been completed.

SUMMARY OF THE INVENTION

The present invention provides a method for producing pyridine bases which comprises reacting in a gas-phase an aliphatic aldehyde, aliphatic ketone or mixture thereof with ammonia in the presence of a zeolite containing titanium and/or cobalt and silicon as zeolite constituent elements in which the atomic ratio of sillcon to titanium and/or cobalt is about 5 to about 1000.

DESCRIPTION OF THE PREFERRED EMBODIMENTS

The production of pyridine bases according to the present invention is conducted by using an aliphatic aldehyde, aliphatic ketone or mixture thereof corresponding to the intended pyridine bases and allowing then to react in a gas-phase with ammonia in the presence of the specific zeolite described above.

The aliphatic aldehyde is preferably an aliphatic aldehyde having 1 to 5 carbon atoms. Examples thereof include saturated aliphatic aldehydes such as formaldehyde, acetaldehyde, propionaldehyde, butylaldehyde and the like, and unsaturated aliphaitic aldehydes such as acrolein, methacrolein, crotonaldehyde and the like. The aliphatic ketone is preferably an aliphatic ketone having 3 to 5 carbon atoms. Examples thereof include acetone, methyl ethyl ketone, diethyl ketone and the like. Dimers, trimers, other oligomers and polymers which generate an aliphatic aldehyde or aliphatic ketone can also be used as the raw material. Relation between the raw material, namely combinations of aliphatic aldehydes and aliphatic ketones, and the main product, namely the pyridine bases, are exemplified in the above-described Table 1.

As described above, a zeolite containing titanium and/or cobalt and silicon as zeolite constituent elements in which the atomic ratio of silicon to titanium and/or cobalt is about 5 to about 1000 and the constraint index is about 0.8 to about 12 is used as the catalyst in the reaction of the present invention. Hereinafter, the above-described zeolite which is used as the catalyst in the present invention is referred to as titan and/or cobaltsilicate zeolite. Examples of the titan and/or cobaltsilicate zeolite include titanosilicates containing titanium and siliccon as zeolite constituent elements, cobaltsilicates containing cobalt and silicon as zeolite constituent elements, and zeolites containing titanium, cobalt and silicon as zeolite constituent elements. One or more of them can be used as the catalyst in the reaction of the present invention. The atomic ratio of silicon to titanium and/or cobalt in the titan and/or cobaltsilicate zeolite used in the present invention is preferably from about 10 to about 500.

The catalyst used in the present invention can be prepared by a conventionally known method. Various titan and/or cobaltsilicate zeolites, which are different from each other in the atomic ratio of silicon to titanium and/or cobalt, crystal structure or the like, can be obtained easily. For example, they can be prepared in the same manner as described in Japanese Patent Application Laid-Open (JP-A) Nos. 63-54358, 60-12135, 56-96720 and 55-7598, Journal of Catalysis, 130, 440 (1991), Applied Catalysis A: General, 126, 51 (1995), Zeolite, 17(4), 354 (1996) and the like.

The crystal structure of the catalyst used in the present invention is not particularly limited, although those having a pentasil type crystal structure are preferable. Among others, those having a MFI type or MEL type crystal structure are more preferable.

In the present invention, a titan and/or cobaltsilicate zeolite can be used as it is, although a titan and/or cobaltsilicate zeolite being allowed to further contain an ion and/or compound of one or more elements selected from group I to XVII elements is preferable, since when it is used, the yield of pyridine bases increases.

The group I to XVII elements are elements listed in the 18-groups type periodic table of element. Specific examples thereof include Li, K, Rb and Cs as group I elements, Mg, Ca, Sr and Ba as group II elements, Sc, Y and lanthanoid elements, La, Ce, Pr, Nd, Er and Yb, as group III elements, Ti, Zr and Hf as group IV elements, V, Nb and Ta as group V elements, Cr, Mo and W as group VI elements, Mn, Tc and Re as group VII elements, Fe, Ru and Os as group VIII elements, Co, Rb and Ir an group IX elements, Ni, Pd and Pt as group X elements, Cu ant Ag as group XI elements, Zn and Cd as group XII elements, Al, Ga, In and Tl as group XIII, Ge, Sn and Pb an group XIV elements, Sb and Bi as group XV elements, Po as group XVI element, and F, Cl as group XVII elements. Among others, Tl and Pb are preferable.

As the ion and/or compound of group I to XVII elements, ions thereof, oxides, halides, sulfates, phosphates, nitrates, hydroxides, sulfides, silicates, titanates, borates and carbonates thereof and the like can be exemplified. One or more of them can be contained in the titan and/or cobaltsilicate zeolite. Examples of the method for allowing a titan and/or cobaltsilicate zeolite to contain these ion and/or compound include an ion exchange method, kneading method, impregnation method, dipping method, deposition method, evaporation drying method and the like, although the method is not limited to these examples. Specific examples thereof are described below.

① An example of ion exchange method

A water soluble salt of the above-described element, such as chloride, nitrate, acetate and the like, is dissolved in water in a concentration of 0.01 to 2 g ion/liter .

Then, an alkali ion form, ammonium ion ($NH_4^+$) form or proton ($H^+$) form titan and/or cobaltsilicate zeolite, preferably a $NH_4^+$ form titan and/or cobaltsilicate zeolite, is added to the aqueous solution obtained above and stirred at a given temperature, then filtrated, and this procedure is repeated.

Thereafter, the finally resulated filtrated residue is washed with water. Thus obtained titan and/or cobaltsilicate zeolite containing an ion of the above-described element is dried, and if necessary, calcined.

② An example of kneading method

A compound of the above-described element is kneaded with a $H^+$ or $NH_4^+$ form titan and/or cobaltsilicate zeolite, if necessary, together with water. Then, the kneaded product is dried, and, if necessary, calcined.

③ An example of dipping method

A water soluble salt of the above-described element is dissolved in water.

Then, a $NH_4^+$ form or $H^+$ form titan and/or cobaltsilicate zeolite, preferably a $NH_4^+$ form titan and/or cobaltsilicate zeolite is dipped in this solution. Thereafter, the dipped zeolite is dried, and if necessary, calcined.

④ An example of deposition method

A $NH_4^+$ form or $H^+$ form titan and/or cobaltsilicate zeolite is dispersed in an aqueous solution of a water soluble salt of the above-described element.

An aqueous ammonia solution is added to this mixture to allow a hydroxide of the above-described element to deposit on the surface of the $NH_4^+$ form or $H^+$ form titan and/or cobaltsilicate zeolite, then filtered.

Thereafter, the filtrated residue is washed with water and dried, and if necessary, calcined.

⑤ An example of evaporation drying method

A compound of the above-described element and a $NH_4^+$ form or $H^+$ form titan and/or cobaltsilicate zeolite are stirred in water to mix them.

Thereafter, an evaporation drying is conducted, then, if necessary, a calcination is conducted.

In any of the above-described methods, the calcination is usually conducted at 350 to 800° C. for several hours under the atmosphere of air, nitrogen and/or carbon dioxide. However, since the catalyst is heated in a reactor during the gas-phase contact reaction, the calcinations of the catalyst is not necessarily required.

The preferable range of content of the ion and/or compound of one or more elements selected from group I to XVII elements varies depending on kind of the titan and/or cobaltsilicate zeolite or kind or form of the element contained therein. Usually, the preferable range is from 0.0005 to 10 mg eq., more preferably from 0.01 to 5, per 1 g of the zeolite containing titanium and/or cobalt and silicon as zeolite constituent elements.

The titan and/or cobaltsilicate zeolite used in the present invention can be molded into a desired shape such as solid cylinder, hollow cylinder and the like by a tablet machine or extruder, as it is or after a binder such as silica, diatomaceous earth, kaolin, bentonite, alumina, silica alumina or the like, and water, polyvinyl alcohol and vinyl acetate is added thereto. The molded article is used as a fixed bed catalyst.

Alternatively, a titan and/or cobaltsilicate zeolite is mixed with a binder such as silica, diatomaceous earth, kaolin, bentonite, alumina, silica alumina or the like, and water to give a slurry, and then the slurry is spray-dried to provide a spherical micro bead, which is used as a fluidized bed catalyst. For producing the titan and/or cobaltsilicate zeolite containing an ion and/or compound of one or more elements selected from group I to XVII elements, a titan and/or cobaltsilicate zeolite which has been molded into a desired shape as described above can be allowed to contain the ion and/or compound by the above-described ion exchange method, impregnation method, dipping method and the like. In any of the above-described methods, the obtained catalyst can be calcined at 350 to 800° C. for several hours under the atmosphere of air, nitrogen, carbon dioxide and the like to give strength to the molded article and to remove volatile components contained in a binder and the like, although, since the catalyst is heated in a reaction vessel during the gas-phase contact reaction, the calcinations of catalyst is not necessarily required.

The production of pyridine bases of the present invention can be conducted in a fixed bed reactor, fluidized bed reactor or moving bed reactor.

An example of methods of the present invention using a fixed bed reactor will be described below.

The catalyst according to the present invention is filled in a reaction tube. A mixed gas of an aliphatic aldehyde and/or aliphatic ketone and ammonia is introduced in this reaction tube, and subjected to a gas-phase reaction. The mixed gas of an aliphatic aldehyde and/or aliphatic ketone and ammonia can also be fed together with water, an inert gas such as nitrogen, and/or methanol.

The combination of an aliphatic aldehyde and/or aliphatic ketone and the suitable use ratio of them to ammonia varies depending on the intended pyridine bases. For example, for producing pyridine and β-picoline as the main products, acetaldehyde and formaldehyde are used as the combination of an aliphatic aldehyde and/or aliphatic ketone, and the molar ratio of acetaldehyde ; formaldehyde; ammonia is preferably 1:0.3–3:0.5–5. In this case, when methanol is used in addition, the amount of methanol is preferably 0.5 mol or less per 1 mol of acetaldehyde. Formaldehyde can be used in the form of a formalin. For producing α-picoline and γ-picoline as the main products, acetaldehyde is used as the combination of an aliphatic aldehyde and/or aliphatic ketone, and the molar ratio of acetaldehyde:ammonia is preferably 1:0.8–3. When acetaldehyde and ammonia are reacted according to the method of the present invention, the selectivity of α-picoline is improved.

A mixed gas of an aliphatic aldehyde, aliphatic ketone and ammonia and, if desired, water, an inert gas such as nitrogen and/or methanol is passed through the catalyst at a space velocity (SV) of 100 to 10000 $hr^{-1}$, preferably 300 to 3000 $hr^{-1}$. The reaction temperature is from 300 to 700° C., preferably from 350 to 600° C. The pressure of the reaction can be from sub-atmospheric pressure to several atoms, although, the reaction pressure from atmospheric pressure to 2 atoms is usually preferable.

After the reaction is conducted as described above, pyridine bases contained in this reaction gas flowing out of the reaction tube may be condensed. Alternatively, it is dissolved in a suitable solvent by allowing the solvent to contact with the reaction gas containing, pyridine bases. The resulted condensate or solution can be distilled to recover pyridines.

When the catalyst deteriorates during a long period of the reaction, it can be regenerated according to a conventional catalyst regeneration method. That is, air is passed through the catalyst layer at a high temperature not exceeding the heat-resistant temperature of the catalyst, preferably at temperatures from 350 to 800° C., to burn carbon deposited on the catalyst. If necessary, the air may be diluted with water vapor, nitrogen, carbon dioxide and the like.

EXAMPLES

The following examples further illustrate the present invention in more specifically, but do not limit the scope of the present invention.

Catalyst Preparation Example 1

Titanosilicate was synthesized as follows according to the method described in Journal of Catalysis, 130, 440 (1991).

Into a pyrex reaction vessel equipped with a stirrer and dropping funnel was charged a mixture of 566 g of a 20% by weight methanol solution of tetra-n-butylammonium hydroxide (n-tetrabutylammonium hydroxide: 0.436 mol) and 455 g (2.18 mol) of tetraethyl orthosilicate. Thereto, 2300 g of a 0.5% by weight isopropyl alcohol solution of tetrabutyl titanate(tetrabutyl titanate: 0.033 mol) was added dropwise from the dropping funnel while mixing, and then stirring was continued for about 30 minutes. To the resulted mixture was added 790 g of distilled water while stirring, and the reaction was continued for 2 hours while removing alcohol at 75–80° C. The resulted reaction mixture was cooled and transferred to an autoclave, and kept at 170° C. for 2 days while stirring. Then, the autoclave was cooled, and the content was filtrated to obtain a crystal. The obtained crystal was washed with ion-exchanged water, dried for 8 hours at 100° C., and then calcined at 550° C. for 16 hours in air flow. The resulted calcined substance was analyzed, and the analysis result shows that it was titanosilicate having a MEL type crystal structure in which Si/Ti (atomic ratio) was 50.

The resulted titanosilicate was added to 1 liter of a 5% aqueous ammonium chloride solution, then stirred at 50 to 60° C. for 1 hour, followed by a filtration, to conduct ion exchange. The residue obtained by the filtration was ion-exchanged three times according to the same manner as described above. The finally resulted residue was washed with water until the concentration of $Cl^-$ ion in the washing liquid became 1 pp or less, and then dried far 16 hours at 110° C. to obtain $NH_4^+$ form titanosilicate. This is further calcined at 550° C. in air for 6 hours to obtain $H^+$ form titanosilicate.

Catalyst Preparation Example 2

Cobaltsilicate was synthesized as follows according to the method described in JP-A-63-54358.

100 g of Tetraethyl orthosilicate (0.48 mol) and 217.5 g of a 10% by weight aqueous solution of tetra-n-propylammonium hydroxide (tetra-n-propylammonium hydroxide: 0.96 mol) were mixed in an autoclave. To the resulted mixture was added a mixed solution of 5.7 g of cobalt (III) acetylacotonate(0.016 mol) and ethylene glycol while stirring, and then stirring was continued for about 30 minutes. Thereafter, the resulted mixture was heated up to 105° C., and stirred for 120 hours at the same temperature to conducted hydrothermal synthesis. The autoclave was cooled, and the content was filtrated to obtain a crystal. The crystal was washed with ion-exchanged water until pH of the washing liquid reached 7.3. The resulted product was dried for 16 hours at 120° C., then calcined at 550° C. for 4 hours in air flow. The calcined substance was analyzed, and the analysis result shows that it was cobaltsilicate having a MFI type crystal structure in which Si/Co (atomic ratio) was 25.

The resulted cobaltsilicate was subjected to ion-exchange, water washing, drying and calcination according to the same manner as in Catalyst Preparation Example 1 to obtain $NH_4^+$ form cobaltsilicate and $H^+$ form cobaltsilicate.

Catalyst Preparation Example 3

Aluminosilicate was synthesized as follows according to the method described in JP-A-2-209867.

433.4 g of Distilled water, 4.6 g of aluminum sulfate, 55.8 g of tetra-n-propylammonium bromide and 40 g of sulfuric acid were mixed to give Solution A. 320 g of Distilled water and 453 g f No. 3 sodium silicate were mixed to give Solution B. 754 g of Distilled water and 189 g of sodium chloride were mixed to give Solution C. Solution C was charged into a stainless autoclave, and to this were added dropwise both of Solutions A and B while stirring vigorously. The mixture was controlled so that pH was kept in the range from 9.5 to 11. The autoclave was sealed and the temperature was raised to 600° C., then stirring was continued to effect hydrothermal synthesis for 20 hours. At this time, the gage pressure was revealed 0.5 to 0.6 Mpa (5 to 6 $kg/cm^2$). After completion of the reaction, the mixture was cooled to room temperature, and the content in the autoclave was filtrated to obtain a crystal produced in the reaction. The crystal was added to distilled water, and stirred and washed, and then filtrated. The above-described washing and filtration were repeated until the Cl⁻ ion concentration in the filtrate became 1 ppm or less. Thereafter, the crystal was dried for 16 hours at 110° C., then, calcined at 530° C. for 4 hours in air flow. The calcined substance was analyzed, and the analysis result shows that it was Na⁺ form aluminosilicate having a MFI type crystal structure in which Si/Al (atomic ratio) was 100.

The resulted Na⁺ form aluminosilicate was subjected to ion-exchange, water washing, drying and calcinations in the same manner as in Catalyst Preparation Example 1, to obtain $NH_4^+$ form aluminosilicate and H⁺ form aluminosilicate.

Catalyst Preparation Example 4

Ferrosilicate was synthesized as follows according to the method described in JP-A-2-209867.

An aqueous solution composed of 19 g of iron (III) nitrate 9-hydrate, 34 g of tetra-n-propylammonium chloride and distilled water was named Solution A. A suspension composed of 70 g of fumed silica and distilled water was named Solution B. A solution composed of 7.4 g of sodium hydroxide and 50 g of distilled water was named Solution C. Solution C was form into a stainless autoclave, and to this was added both of Solutions A and B while stirring to mix them. The autoclave was sealed and the temperature was raised to 160° C., then stirring was continued to effect hydrothermal synthesis for 60 hours. pH was changed from 12.4 to 11.4. The content in the autoclave was filtrated to obtain a solid. The solid was washed with distilled water until pH of the washing solution reached 7.3. The resulted solid was analyzed and the analysis result shows that it was Na⁺ form ferrosilicate having a MFI type crystal structure in which Si/Fe (atomic ratio) was 25.

The resulted Na⁺ form ferrosilicate was subjected to ion-exchange, water washing, drying and calcinations in the same manner as in Catalyst Preparation Example 1 to obtain $NH_4^+$ form ferrosilicate and H⁺ form ferrosilicate.

Catalyst Preparation Example 5

Na⁺ form gallosilicate, $NH_4^+$ form gallosilicate and H⁺ form gallosilicate were obtained according to the same manner as in Catalyst Preparation Example 4 except that 19 g of gallium (III) nitrate 8-hydrate was used instead of iron (III) nitrate 9-hydrate used in Catalyst Preparation Example 4. Na⁺ form gallosilicate was analyzed, and the analysis result shows that it had a MFI type crystal structure and Si/Ga (atomic ratio) was 25.

Example 1

H⁺ form titanosilicate (H⁺ form Ti/Si) obtained in Catalyst Preparation Example 1 was compressed at a pressure of 39 Mpa, then, ground to obtain particles having uniformed particle sizes from 1.0 to 1.7 mm (10 to 16 mesh). A production of pyridine bases was conducted using these particles as the catalyst according to the following manner.

6 g of the Catalyst obtained above was filled in a glass reaction tube having an internal diameter of 20 mm. The catalyst filled part of the reaction tube was heated at 380° C., and 2760 ml/hr of ammonia gas and 2.48 g/hr of acetaldehyde were fed to this catalyst filled part. After 30 minutes from initiation of the feeding of acetaldehyde, the reaction gas flowing out of the reaction tube was bubbled into water for 20 minutes to dissolve soluble components in the reaction gas into water. The resulted solution was analyzed by gas chromatography. The results are shown in Table 3.

The yield of pyridine bases was based on the total carbon number of the acetaldehyde subjected to the reaction, and calculated according to the following calculation formulae.

Pyridine yield (%)=[(Total carbon atom number of produced pyridine)/(Total carbon atom number of acetaldehyde subjected to the reaction)]×100

α, β or γ-Picoline yield (%)=[(Total carbon atom number of produced α, β or γ-picoline)/(Total carbon atom number of acetaldehyde subjected to the reaction)]×100

Example 2

A production of pyridine bases was conducted according to the same manner as in Example 1, except that the H⁺ form cobaltsilicate (H⁺ form Co/Si) obtained in Catalyst Preparation Example 2 was used instead of the H⁺ form titanosilicate used in Example 1. The results are shown in Table 3.

Comparative Example 1

A production of pyridine bases was conducted according to the same manner as in Example 1, except that the H⁺ form aluminosilicate (H⁺ form Al/Si) obtained in Catalyst Preparation Example 3 was used instead of the H⁺ form titanosilicate used in Example 1. The results are shown in Table 3.

Comparative Example 2

A production of pyridine bases was conducted according to the same manner as in Example 1, except that the H⁺ form ferrosilicate (H⁺ form Fe/Si) obtained in Catalyst Preparation Example 4 was used instead of the H⁺ form titanosilicate used in Example 1. The results are shown in Table 3.

Comparative Example 3

A production of pyridine bases was conducted according to the same manner as in Example 1, except that the H⁺ form gallosilicate (H⁺ form Ga/Si) obtained in Catalyst Preparation Example 5 was used instead of the H⁺ form titanosilicate used in Example 1. The results are shown in Table 3.

TABLE 3

| | | Yield (%) | | | | |
| --- | --- | --- | --- | --- | --- | --- |
| No. | Catalyst | Py | αPc | βPc | γPc | Total |
| Example 1 | H⁺ form Ti/Si | 1.2 | 34.2 | 0 | 12.1 | 47.5 |
| Example 2 | H⁺ form Co/Si | 1.6 | 27.0 | 0 | 12.8 | 41.4 |
| Comparative example 1 | H⁺ form Al/Si | 5.1 | 17.6 | 0 | 18.5 | 41.2 |
| Comparative example 2 | H⁺ form Fe/Si | 3.2 | 18.6 | 0 | 17.5 | 39.3 |
| Comparative example 3 | H⁺ form Ga/Si | 2.5 | 17.3 | 0 | 19.3 | 39.1 |

Py: Pyridine yield
αPc: α-Picoline yield
βPc: β-Picoline yield
γPc: γ-Picoline yield Example 3

Into a solution prepared by dissolving 1.68 g of lead nitrate into 18.14 g of water was added 13.93 g of H⁺ form titanosilicate obtained in Catalyst Preparation Example 1 to be impregnated. The resulted product was dried at 120° C. for 5 hours, then, calcined at 550° C. for 5 hours in air flow, to obtain titanosilicate containing Pb in an amount of 7% by weight in terms of metal (0.73 mg eq. per 1g of titanosilicate).

Production of pyridine bases was conducted in the same manner as in Example 1 except that the Pb-containing titanosilicate (7% Pb—Ti/Si) obtained above was used instead of H⁺ form titanosilicate used in Example 1. The results are shown in Table 4.

Example 4

Into a solution prepared by dissolving 0.96 g of lead nitrate into 14.2 g of water was added 19.4 g of H⁺ form cobaltsilicate obtained in Catalyst Preparation Example 2, and they were mixed. The resulted mixture was dried at 120° C. for 5 hours, then, calcined at 550° C. for 5 hours in air flow, to obtain cobaltsilicate containing Pb in an amount of 3% by weight in terms of metal (0.30 mg eq. per 1 g of cobaltsilicate).

Production of pyridine bases was conducted in the same manner as in Example 1 except that the Pb-containing cobaltsilicate (3% Pb—Co/Si) obtained above was used instead of H⁺ form titanosilicate used in Example 1. The results are show in Table 4.

Example 5

Into a solution prepared by dissolving 59.54 g of ammonium tungstate para[5(NH$_4$)$_2$O·12WO$_3$·5H$_2$O] into 200 g of water was added 7.44 g of H⁺ form cobaltsilicate obtained in Catalyst Preparation Example 2, and they were mixed. The resulted mixture was dried at 120° C. for 5 hours, then, calcined at 550° C. for 5 hours in air flow, to obtain cobaltsilicate containing W in an amount of 7% by weight in terms of metal(2.46 mg eq. per 1 g of cobaltsilicate).

Production of pyridine bases was conducted in the same manner as in Example 1 except that the cobaltsilicate containing W (7% W—Co/Si) obtained above was used instead of H⁺ form titanosilicate used in Example 1. The results are shown in Table 4.

Example 6

Into a solution prepared by dissolving 2.55 g of zinc nitrate 6-hydrate into 10.4 g of water was added 7.44 g of H⁺ form cobaltsilicate obtained in Catalyst Preparation Example 2, and they were mixed. The resulted mixture was dried at 120° C. for 5 hours, then, calcined at 550° C. for 5 hours in air flow, to obtain cobaltsilicate containing Zn in an amount of 7% by weight in terms of Metal(2.30 mg eq. per 1 g of cobaltsilicate).

Production of pyridine bases was conducted in the same manner as in Example 1 except that the cobaltsilicate containing Zn (7% Zn—Co/Si) obtained above was used instead of H⁺ form titanosilicate used in Example 1. The results are shown in Table 4.

Example 7

Into a solution prepared by dissolving 0.73 g of thallium (I) nitrate into 10.4 g of water was added 7.44 g of H⁺ form cobaltsilicate obtained in Catalyst Preparation Example 2, and they were mixed. The resulted mixture was dried at 120° C. for 5 hours, then, calcined at 550° C. for 5 hours in air flow, to obtain cobaltsilicate containing Tl in an amount of 7% by weight in terms of metal(0.37 mg eq. per 1 g of cobaltsilicate).

Production of pyridine bases was conducted in the same manner as in Example 1 except that the cobaltsilicate containing Tl (7% Tl—Co/Si) obtained above was used instead of H⁺ form titanosilicate used in Example 1. The results are shown in Table 4.

Example 8

Into a solution prepared by dissolving 1.75 g of lanthanum nitrate 6-hydrate into 10.4 g of water was added 7.44 g of H⁺ form cobaltsilicate obtained in Catalyst Preparation Example 2, and they were mixed. The resulted mixture was dried at 120° C. for 5 hours, then, calcined at 550° C. for 5 hours in air flow, to obtain cobaltsilicate containing La in an amount of 7% by weight in terms of metal(1.63 mg eq. per 1 g pf cobaltsilicate).

Production of pyridine bases was conducted in the same manner as in Example 1 except that the cobaltsilicate containing La (7% La—Co/Si) obtained above was used instead of H⁺ form titanosilicate used in Example 1. The results are shown in Table 4.

Example 9

Into a solution prepared by dissolving 3.32 g of indium sulfate 9-hydrate into 10.4 g of water was added 7.44 g of H⁺ form cobaltsilicate obtained in Catalyst Preparation Example 2, and they were mixed. The resulted mixture was dried at 120° C. for 5 hours, then, calcined at 550° C. for 5 hours in air flow, to obtain cobaltsilicate containing In in an amount of 7% by weight in terms of metal(1.97 mg eq. per 1 g of cobaltsilicate).

Production of pyridine bases was conducted in the same manner as in Example 1 except that the cobaltsilicate containing In (7% In—Co/Si) obtained above was used instead of H⁺ form titanosilicate used in Example 1. The results are shown in Table 4.

TABLE 4

| No. | Catalyst | Yield (%) | | | | |
|---|---|---|---|---|---|---|
| | | Py | αPc | βPc | γPc | Total |
| Example 3 | 7% Pb—Ti/Si | 1.1 | 52.1 | 0 | 17.0 | 70.2 |
| Example 4 | 3% Pb—Co/Si | 1.1 | 51.6 | 0 | 20.1 | 72.8 |
| Example 5 | 7% W—Co/Si | 1.0 | 28.0 | 0 | 15.5 | 44.5 |
| Example 6 | 7% Zn—Co/Si | 1.0 | 34.9 | 0 | 17.2 | 53.1 |
| Example 7 | 7% Tl—Co/Si | 0.9 | 38.5 | 0 | 14.4 | 53.8 |
| Example 8 | 7% La—Co/Si | 1.8 | 29.9 | 0 | 11.8 | 43.5 |
| Example 9 | 7% In—Co/Si | 1.8 | 29.9 | 0 | 11.8 | 43.5 |

Py: Pyridine yield
αPc: α-Picoline yield
βPc: β-Picoline yield
γPc: γ-Picoline yield

What is claimed is:

1. A method for producing pyridine bases which comprises reacting in a gas-phase an aliphatic aldehyde, aliphatic ketone or mixture thereof with ammonia in the presence of a zeolite containing silicon and at least one member from the group consisting of titanium and cobalt, as zeolite constituent elements in which the atomic ratio of silicon to titanium and/or cobalt is about 5 to about 1000.

2. The method for producing pyridine bases according to claim 1 wherein the aliphatic aldehyde and aliphatic ketone are an aliphatic aldehyde having 1 to 5 carbon atoms and an aliphatic ketone having 3 to 5 carbon atoms, respectively.

3. The method for producing pyridine bases according to claim 1 wherein the atomic ratio of silicon to titanium and/or cobalt is about 10 to about 500.

4. The method for producing pyridine bases according to claim 1 wherein the zeolite containing titanium and/or cobalt and silicon as zeolite constituent elements has a pentasil type crystal structure.

5. The method for producing pyridine bases according to claim 1 wherein the zeolite containing titanium and/or cobalt and silicon as zeolite constituent elements has a MFI type or MEL type crystal structure.

6. The method for producing pyridine bases according to claim 1 wherein the zeolite containing titanium and/or cobalt and silicon as zeolite constituent elements is allowed to further contain an ion and/or compound of one or more elements selected from group I to XVII elements.

7. The method for producing pyridine bases according to claim 6 wherein content of the ion and/or compound of one or more elements selected from group I to XVII elements is from 0.0005 to 10 mg eq. per 1 g of the zeolite containing titanium and/or cobalt and silicon as zeolite constituent elements.

8. The method for producing pyridine bases according to claim 1 wherein the aliphatic aldehyde, aliphatic ketone or mixture thereof is acetaldehyde.

\* \* \* \* \*